(12) United States Patent
Cosgrove et al.

(10) Patent No.: US 8,816,005 B2
(45) Date of Patent: Aug. 26, 2014

(54) SOLVENT-FREE SYNTHESIS OF AMPHIPHILIC POLYMERIC MATERIAL

(75) Inventors: Terence Cosgrove, Portishead (GB);
Roger Pettman, Marco Island, FL (US);
Erol Hasan, Liverpool (GB)

(73) Assignee: Revolymer Limited, London (GB)

( * ) Notice: Subject to any disclaimer, the term of this patent is extended or adjusted under 35 U.S.C. 154(b) by 498 days.

(21) Appl. No.: 12/733,698

(22) PCT Filed: Oct. 15, 2008

(86) PCT No.: PCT/EP2008/063879
§ 371 (c)(1),
(2), (4) Date: Apr. 12, 2010

(87) PCT Pub. No.: WO2009/050203
PCT Pub. Date: Apr. 23, 2009

(65) Prior Publication Data
US 2010/0233314 A1    Sep. 16, 2010

(30) Foreign Application Priority Data

| Oct. 15, 2007 | (EP) | 07118487 |
|---|---|---|
| Nov. 26, 2007 | (EP) | 07121564 |
| Feb. 26, 2008 | (WO) | PCT/EP2008/052325 |
| Feb. 26, 2008 | (WO) | PCT/EP2008/052326 |
| Jun. 5, 2008 | (EP) | 08157683 |
| Jun. 5, 2008 | (EP) | 08157684 |

(51) Int. Cl.
| C08F 8/10 | (2006.01) |
|---|---|
| C07B 51/00 | (2006.01) |
| C08G 63/91 | (2006.01) |
| C08F 8/32 | (2006.01) |
| C08F 236/02 | (2006.01) |

(52) U.S. Cl.
CPC ... *C08F 8/10* (2013.01); *C08F 8/32* (2013.01);
*C08F 236/02* (2013.01); *C07B 51/00* (2013.01);
*C08G 63/91* (2013.01)
USPC ............ 525/69; 525/79; 525/379; 525/384

(58) Field of Classification Search
CPC ............ C08F 8/10; C08F 8/32; C08F 236/02;
C07B 51/00; C08G 63/91
USPC .................. 525/55, 69, 79, 379, 384; 526/75
See application file for complete search history.

(56) References Cited

U.S. PATENT DOCUMENTS

| 4,241,091 A | 12/1980 | Stroz et al. |
|---|---|---|
| 5,336,509 A | 8/1994 | McGrew et al. |
| 6,986,907 B2 | 1/2006 | Phillips et al. |
| 2005/0084466 A1 | 4/2005 | Mullay et al. |

FOREIGN PATENT DOCUMENTS

| EP | 0 945 473 A1 | 9/1999 |
|---|---|---|
| EP | 945473 A1 * | 9/1999 |
| GB | 1025958 | 4/1966 |
| WO | WO 99/31994 A1 | 7/1999 |
| WO | WO 99/31995 A1 | 7/1999 |
| WO | WO 2006/016179 A1 | 2/2006 |

OTHER PUBLICATIONS

International Search Report issued in International Application No. PCT/EP2008/063879 by the International Bureau on Jan. 19, 2009.
Fritz, "Formulation and Production of Chewing and Bubble Gum," Kennedy's Publications Ltd, 2006, ISBN: 0-0904725-10-3 (9 pages).
Collins English Dictionary, Third Edition, 1994, pp. 128 and 280-281.

* cited by examiner

*Primary Examiner* — Kelechi Egwim
(74) *Attorney, Agent, or Firm* — Oliff PLC

(57) ABSTRACT

The present invention provides a method for making a composition comprising an amphiphilic polymeric material which comprises a straight or branched chain carbon-carbon backbone and a multiplicity of side chains attached to the backbone; wherein in the method, backbone precursors comprising acylating groups are mixed with side chain precursors which comprise a nucleophilic group at at least one terminus, to form a reaction mixture; the backbone precursors, side chain precursors and/or the reaction mixture are heated; the reaction mixture is stirred; and the nucleophilic groups react with the acylating groups to form the amphiphilic polymeric material wherein the side chains are linked to the backbone via acyl linkages; characterized in that the reaction mixture does not comprise organic solvent.

18 Claims, 6 Drawing Sheets

SOLVENT-FREE SYNTHESIS OF AMPHIPHILIC POLYMERIC MATERIAL

Figure 1:
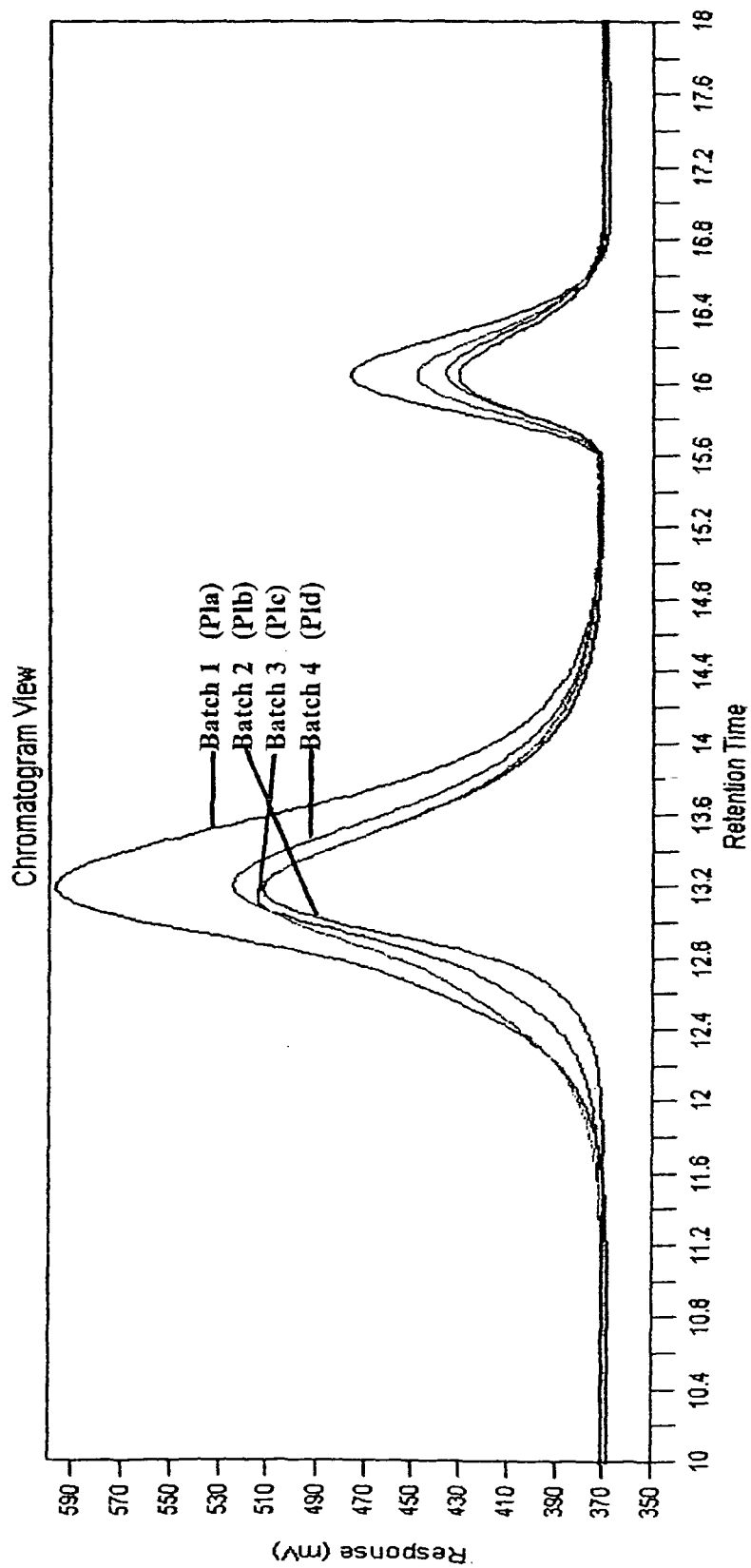

The present invention relates to a method for the production of an amphiphilic polymeric material wherein no solvent is used.

Chewing Gum is a consumer good that is regularly enjoyed by millions of people worldwide. We have disclosed, in our previous Patent application published as WO2006/016179 that the addition of an amphiphilic graft copolymer to chewing gum formulations can result in them having reduced stickiness, combating the problems associated with pollution resulting from carelessly discarded gum cuds. In that Patent application, the graft copolymer is formed by reacting polyisoprene-graft-maleic anhydride (the backbone) with poly(alkyleneoxy) alcohol side chain precursors in an organic solvent such as toluene and typically in the presence of an activator, for instance, triethylamine at elevated temperature.

As gum is a commodity product it is desirable to ensure that the synthesis of any of the ingredients is efficient to ensure that the cost of the resulting material is as competitive as possible.

In accordance with this desire, there is provided in a first aspect of the invention a method for making a composition comprising an amphiphilic polymeric material which comprises a straight or branched chain carbon-carbon backbone and a multiplicity of side chains attached to the backbone;

wherein in the method, backbone precursors comprising acylating groups are mixed with side chain precursors which comprise a nucleophilic group at at least one terminus to form a reaction mixture;

the backbone precursors, side chain precursors and/or the reaction mixture are heated;

the reaction mixture is stirred;

and the nucleophilic groups react with the acylating groups to form the amphiphilic polymeric material wherein the side chains are linked to the backbone via acyl linkages; characterised in that the reaction mixture does not comprise organic solvent such as toluene.

In a second aspect of the invention, there is provided a method for making a comestible comprising making a composition comprising an amphiphilic polymeric material according to the first aspect of the invention, and adding the composition to a comestible.

In a third aspect of the invention there is provided a composition comprising an amphiphilic polymeric material which comprises a straight or branched chain carbon-carbon backbone, and a multiplicity of side chains attached to the backbone, and optionally, backbone precursors comprising acylating groups and side chain precursors comprising nucleophilic groups characterised in that the composition comprises no organic solvent; obtainable by a method according to the first aspect of the invention.

In a fourth aspect of the invention, there is provided a composition comprising an amphiphilic polymeric material (a) which comprises a straight or branched chain carbon-carbon backbone, and a multiplicity of side chains attached to the backbone, and optionally, backbone precursors comprising acylating groups; and side chain precursors (b) comprising nucleophilic groups;

wherein the weight ratio of (a):(b) is in the range 1:0 to 1:1; characterised in that the composition comprises no organic solvent.

The invention outlined herein involves the strategy of minimising or eliminating the use of undesirable materials that were previously required to create the polymeric material. More specifically, this is achieved by eliminating the use of solvent. Smaller amounts of the side chain precursors can also be used. In addition, purification at the end of the reaction to remove solvent is advantageously no longer required. The resultant amphiphilic polymeric material retains all of the qualities associated with material made using the traditional solvent route—i.e. the material is of low tack and can be incorporated into chewing gum compositions to reduce their adhesive nature.

This solvent-free process eliminates the costs associated with purchasing and handling organic solvents, and removing the otherwise harmful materials from the resultant polymeric material. It will be appreciated that this approach is also desirable in eliminating volatile organic compounds that may be harmful to the environment.

Solvent-free methods for making compositions containing anhydride based graft copolymers are known. EP0945473, for instance, describes such a method which involves mixing an ethylenically-unsaturated monomer, an anhydride monomer, and either a monofunctional polyglycol having a hydroxyl or amine terminal group or a polyfunctional polyglycol, and a free radical initiator to form a mixture. The mixture is heated to form a mixture of graft copolymeric materials of the polyglycol and the ethylenically unsaturated monomer including the graft copolymer product, which may be useful as a soil release agent in detergent formulations.

The present invention differs from the disclosure in EP0945473, in that the method in the latter results in a multitude of different products. The presently to claimed method avoids this problem by reacting a pre-formed polymeric backbone with side chain precursors. Furthermore, the present method does not proceed via a free-radical mechanism.

The synthesis of the amphiphilic polymeric material is achieved by mixing the intended side chain precursors with the backbone precursors. The side chain and backbone precursors may be either a solid, in fluid form, a liquid or a gel, when they are added to the reaction mixture, provided that they can be mixed fairly efficiently. More preferably they will be either a liquid or finely ground solid. Most preferably they will both be a liquid at the temperature at which the acylation reaction takes place. Alternatively, the side chain precursors are liquid and the backbone precursors are a finely ground solid.

In one preferred embodiment of the invention, the backbone precursors are mixed with the side chain precursors by dissolving the backbone precursors in molten side chain precursors. Alternatively, side chain precursors may be dissolved in molten backbone precursors.

It will be appreciated by those skilled in the art that the reaction process may be performed using any piece of equipment that is capable of providing sufficient mixing. These may include reactors or other any vessels where agitation is provided by an overhead stirrer, a magnetic stirrer, most preferably mixing is achieved using an appropriate an extruder, z-blade mixer, batch mixer, U trough mixer, RT mixer, compounder, internal mixer, Banbury type mixer, two roll mill, Brabender type mixer, a wide blade mixer (or hydrofoil blade mixer), horizontal (delta or helical) blade mixer, kneader-reactor, or a related variation of one of these mixers such as such as a double z-blade mixer or twin screw extruder.

The reaction mixture is typically stirred for between 30 minutes to 48 hours, more typically for 1 hour to 24 hours, most typically for between 4 hours to 12 hours, for instance, around 6 hours.

Increasing the temperature of the reaction mixture generally results in the side chain precursors melting, which allows efficient mixing, and in turn contributes to an increase in the rate of reaction. Therefore the temperature of the reaction will preferably be between 50° C. and 300° C., more preferably between 100 and 250° C., even more preferably between 115° C. and 200° C., for instance, between 120° C. and 200° C., and most preferably between 140° C. and 180° C. Whilst too low a temperature might lead to the products being insufficiently mixed, too high will lead to cross-linking. Generally the reaction mixture is heated to this temperature and maintained at this temperature, with stirring, for at least 6 hours, typically at least 12 hours and preferably for least 24 hours.

Generally, the backbone and side chain precursors are heated to such temperatures after being mixed to form the reaction mixture. It is possible that the precursors may be pre-heated and then added to a reactor at a temperature suitable for the reaction.

Preferably the mixing apparatus is supplied with an inert gas to prevent degradation of the polymeric materials. Alternatively the reactor may be placed under vacuum in order to ensure that air is excluded. The reaction can also be catalysed by addition of acid or base. Optionally water may be added to the reactor at the end of the reaction to hydrolyse any unreacted acylating groups. Hydrolysis of unreacted acylating groups can also advantageously increase the hydrophilicity and thus water compatibility or solubility of the materials.

At the end of the acylation reaction (which may also be referred to as the grafting reaction) any remaining acylating groups may be converted into acid groups by the addition of water to the material, or by an aging process. Alternatively the remaining acylating groups may be hydrolysed using water and a base as catalyst, or by the addition of an alcohol (hydroxyl) or amine with or without base. By way of an example, any remaining maleic anhydride groups are typically converted into diacid groups by addition of water to the material.

The product mixture, at the end of the reaction, normally comprises unreacted starting materials which may include free side chain precursors, by-products and catalyst (if used in the reaction). The amphiphilic polymeric material need not be purified from the reaction mixture, since it can be advantageous to have free side chain precursor in the final composition. The free side chain precursor may interact with the amphiphilic polymeric material and thereby improve its properties. Preferably, in the composition according to the fourth aspect of the invention, the ratio of (a):(b) is in the range 3:2 to 5:1, more preferably 3:2 to 4:1.

The backbone precursor used to make the polymeric material in this invention is preferably derived from a homopolymer of an ethylenically unsaturated hydrocarbon monomer or from a copolymer of two or more ethylenically unsaturated hydrocarbon monomers. The backbone precursor is typically an elastomeric material. The amphiphilic polymeric material may also be an elastomeric material.

The backbone precursor typically comprises a homopolymer of an ethylenically-unsaturated polymerisable hydrocarbon monomer or a copolymer of two or more ethylenically-unsaturated polymerisable hydrocarbon monomers. By the term "ethylenically-unsaturated polymerisable hydrocarbon monomer" we mean a polymerisable hydrocarbon containing at least one carbon-carbon double bond which is capable of undergoing addition (otherwise known as chain-growth or chain-reaction) polymerisation to form a straight or branched chain hydrocarbon polymer having a carboncarbon polymer backbone. According to one preferred embodiment, the backbone precursor comprises a homopolymer of an ethylenically-unsaturated polymerisable hydrocarbon monomer containing 4 or 5 carbon atoms, for example, isobutylene (2-methylpropene). The carbon-carbon polymer backbone precursor may also, according to another embodiment, be derived from a homopolymer of a conjugated diene hydrocarbon monomer, especially one containing 4 or 5 carbon atoms, such as 1,3-butadiene or isoprene.

As mentioned above, the carbon-carbon polymer backbone precursor may comprise a copolymer of two or more ethylenically-unsaturated polymerisable hydrocarbon monomers. Preferably, it comprises a copolymer of two such monomers. For example, it may comprise a hydrocarbon copolymer of a hydrocarbon monomer having one carbon-carbon double bond and a hydrocarbon monomer having two carbon-carbon double bonds. For example, the carbon-carbon polymer backbone may comprise a copolymer of isobutylene and isoprene. According to a different embodiment, the carbon-carbon polymer backbone is derived from a butadiene-styrene block copolymer. The backbone may comprise a random, alternating or block, e.g. A-B or AB-A block copolymer.

Alternatively, the backbone precursor may comprise a copolymer of at least one ethylenically-unsaturated monomer and maleic anhydride. The term copolymer covers both bipolymers and terpolymers. Preferably the monomer is a hydrocarbon monomer. By the term "ethylenically-unsaturated polymerisable hydrocarbon monomer" we mean a polymerisable hydrocarbon containing at least one carbon-carbon double bond which is capable of undergoing polymerisation to form a straight or branched chain hydrocarbon polymer having a carbon-carbon polymer backbone. According to one preferred embodiment, the ethylenically-unsaturated polymerisable hydrocarbon monomer contains 4 or 5 carbon atoms, and is, for instance, isobutylene (2-methylpropene). The ethylenically unsaturated monomer may alternatively be a conjugated diene hydrocarbon monomer, especially one containing 4 or 5 carbon atoms, such as 1,3-butadiene or isoprene. The ethylenically-unsaturated monomer may alternatively be 1-octadecene.

In this aspect of the invention, the ethylenically unsaturated monomer may be aromatic and/or contains atoms other than hydrogen and carbon. Suitable ethylenically unsaturated monomers include styrene and vinyl methyl ether.

The backbone precursor typically has a molecular weight in the range 10,000 to 200,000, preferably 15,000 to 50,000, more preferably from 20,000 to 40,000. Unless otherwise specified, the unit of molecular weight used in this specification is g/mol.

The backbone precursor may comprise acylating groups in the backbone, or grafted onto the backbone. The backbone precursor typically has units derived from maleic anhydride grafted thereon. One suitable backbone precursor is polyisoprene grafted with maleic anhydride (PIP-g-MA). Such graft copolymers are commercially available, as detailed below, or can be synthesised.

The backbone precursor is typically hydrophobic in nature. In contrast, the side chain precursors may be hydrophilic. This confers several advantages. The hydrophobic/hydrophilic balance of the resultant amphiphilic polymeric material has a comb-like copolymer structure which gives the material its low-tack properties. The hydrophilic side chains confer surface active properties on the polymeric material.

The hydrophilic side chain precursors used in this invention preferably comprise poly(alkylene oxide), polyglycidol, poly(vinyl alcohol), poly(styrene sulphonate) or poly(acrylic acid), most preferably poly(ethylene oxide), having at least one nucleophilic group at each terminus. Alternatively, the side chains may be derived from a polypeptide, for example polylysine.

Alternatively, the side chains of the polymeric material may be more hydrophobic than the backbone. Suitable examples include fluoroalkanes, polysilanes, polyalkylsilanes, alkylsilyl polyoxyalkylenes and siloxanes, which impart a very low surface energy to the gum base.

The molecules of backbone in the amphiphilic polymeric material may have a plurality of side chains which may include a mixture of the side chains listed above, and/or have different chain lengths/molecular weights. Preferably, however, each side chain has the same chain length/molecular weight.

Preferably, the acylating groups of the backbone precursors are acid anhydride groups, typically derived from maleic anhydride. Other possible acylating groups include carboxylic acids, acid amides, acyl chlorides and carboxylic acid esters.

Preferably, the nucleophilic groups of the side chain precursors are amine or hydroxyl groups.

Preferably, the side chains in the polymeric material have the formula (I)

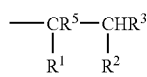 (I)

wherein $R^1$ and $R^2$ are each, independently H, —C(O)WR$^4$ or —C(O)Q;

provided that at least one of $R^1$ and $R^2$ is the group —C(O)Q;

or $R^1$ and $R^2$ together form a cyclic structure together with the carbon atoms to which they are attached, of formula (II)

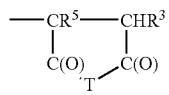 (II)

$R^3$-$R^5$ are each, independently, H or $C_{1-6}$ alkyl;
W is O or NR$^4$;
Q is a group of formula —X$^1$—Y—X$^2$—P;
T is a group of formula N—Y—X$^2$—P;
wherein X$^1$ is NR$^4$, S or O;
X$^2$ is O, S, (CH$_2$)$_n$ or NR$^4$; wherein n is 1-6;
P is H or another backbone; and
Y is a hydrophilic polymeric group.
Preferably, $R^2$ is —C(O)WR$^4$ or —C(O)Q. $R^3$ is preferably H or —CH$_3$. $R^5$ is typically H. X$^1$ and X$^2$ are each, independently, preferably NR$^4$ or O. n is preferably 1-4.

According to one embodiment of the present invention, the side chains in the polymeric material have the formula

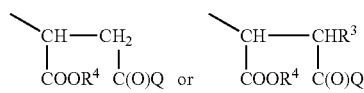

wherein $R^3$, $R^4$ and Q are as defined above. These groups are derived from maleic anhydride units or derivatives thereof grafted onto the backbone.

Preferably, the polymeric material has pendant carboxylic acid groups. In the above formula therefore, preferably $R^4$ is H.

According to another embodiment, the side chains may have formula

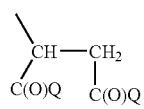

wherein Q is as defined above.

In another embodiment the side chains have the following formula

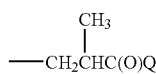

wherein Q is as defined above. These are derived from methacrylic-grafted materials.

According to another embodiment the side chains may have the formula

—CH$_2$CH$_2$C(O)Q

These are derived from acrylic grafted materials.

Two polymeric materials which may be produced using the novel method are detailed in Table 1 below. Two particularly preferred polymeric materials are P(A) and P(B).

TABLE 1

Polymeric materials

| Name | Backbone Precursor | Side Chain Precursor |
|------|-------------------|---------------------|
| P(A) | PIP-g-MA          | PEO 2K              |
| P(B) | PIP-g-MaMme       | PEO 2K              |

PIP = polyisoprene;
g = graft;
MA = maleic anhydride;
MaMme = Monoacid monomethyl ester;
PEO = polyethylene oxide and
K = 1000 molecular weight units.

Any PIP-g-MA of appropriate molecular weight distribution and maleic anhydride content will be suitable for the synthesis of the polymeric material. Alternatively carboxylated PIP-g-MA materials in which the maleic anhydride is ring opened to form a diacid or mono-acid/mono-methyl ester will also be suitable. The latter is demonstrated in P(B).

The backbone precursors of these polymeric materials are derived from polyisoprene to which maleic anhydride has been grafted. The level of grafting of MA is typically around 1.0 mol % in the PIP-g-MA used to demonstrate the concept. In PIP-g-MaMme the same level was 2.7 mol % of the monoacid mono-methyl ester of MA. The level of grafting depends on the degree of functionalisation of the polyisoprene. For example, in P(A) the number of grafts per chain is generally between 1 and 7, whereas in P(B) it is between 1 and 10.

In the method according to this invention, generally 1-4, more typically between 2 and 3 equivalents of side chain precursors with respect to each maleic anhydride group should be reacted. Reaction efficiency may be increased by reacting the PIP-g-MA used to synthesize P(A) with side chain precursors which are polyether amines. These are available commercially; a range of mono and difunctionalised amine polymers of ethylene oxide (EO) and propylene oxide (PO) are sold under the Jeffamine brand name by Huntsman. Reaction between the amine functionalized polymers with maleic anhydride, for instance, can generate any of the following structures:

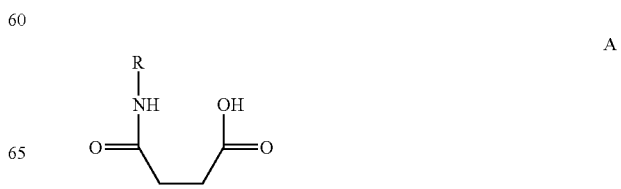

A

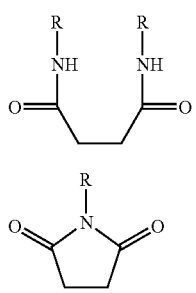

The structure marked C is formed by an intramolecular reaction of A, accompanied by the elimination of H₂O, is more likely to occur with the assistance of a catalyst for instance an acid. Both mono and difunctional amine polymers are used in the invention; reaction of a hydrophobic backbone with a hydrophilic amine functionalised polymer will lead to the synthesis of an amphiphilic graft copolymer. Depending on the reaction conditions, the use of hydrophilic difunctional amine polymers will lead to a cross-linked or chain extended polymer. Alternatively mono and difunctional polymers may be combined to modify the properties of the resulting polymeric material to that required. Jeffamine M-1000 and M-2070 are particularly preferred, side chain precursors.

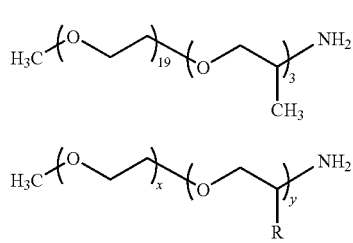

[x=6, y≈35 where R is a mixture of H for (EO), or CH₃ for (PO) units]

Jeffamine M-1000 is a monoamine polyether with a EO:PO ratio of 19:3 and a molecular weight of approximately 1000; M-2070 is a monoamine polyether with an EO:PO ratio of 31:10 and a molecular weight of approximately 2000. Due to the relatively high ratios of ethylene oxide units in these polymers they are regarded as hydrophilic materials. Both M-1000 and M-2070 have been found to react efficiently with PIP-g-MA.

It is also possible to synthesise graft copolymers through the reaction of amine functionalised polyethers with a monoester of maleic anhydride, for instance we have obtained good results with a PIP-g-MaMme (polyisoprene-graft-monoacid monomethyl ester supplied by Kuraray Co. Ltd, sold as LIR-410) with the general formula

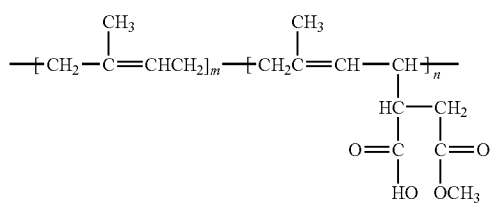

and has a functionality (i.e. n) of approximately 10, an average molecular weight of about 25,000, and a glass transition temperature of −59° C. Each monomethyl ester may react with a single amine functionality.

As stated above, the properties of the polymeric material depend not only on the character of the side chains grafted onto the carbon-carbon polymer backbone but also on the number of grafted side chains. In the invention a multiplicity of side chain precursors react with each backbone precursor. The term "multiplicity" is defined herein as meaning one or more grafted side chains, and generally means two or more. Typically, at least one side chain precursor reacts with each backbone precursor. In order to achieve a desired degree of hydrophilicity in the polymeric material, it is preferred that the ratio of side chains to backbone units in the resultant polymeric material is in the range 1:400 to 1:5, but more preferably 1:200 to 1:10. The side chains are typically statistically distributed along the carbon-carbon polymer backbone since the location of attachment of the side chain on the backbone will depend on the positions of suitable attachment locations in the backbone of the hydrocarbon polymer used in the manufacture.

When the side chains are linked to the polymer backbone via grafted maleic anhydride units, each maleic anhydride unit in the polymer backbone may be derivatised with either zero, one or two side chains.

In one embodiment of the invention, each side chain precursor has two nucleophilic groups which may react with two acylating groups on different backbone precursors, thereby forming a cross-linked structure. For instance, a polyethylene glycol side chain is generally terminated with an alcohol at each end, before derivatisation. Each alcohol may be grafted onto a backbone maleic anhydride unit.

When the backbone precursor of the amphiphilic polymeric material is a copolymer of maleic anhydride together with an ethylenically-unsaturated monomer, side chain precursors are typically terminated by an alcohol or amine nucleophilic group at one end and an alkyloxy group at the other. MeO-PEO-OH is an example of a preferred side chain precursor. In the method of formation of the polymeric material such side chains react with the maleic anhydride derived units via alcoholysis of the anhydride to give a carboxylic ester and carboxylic acid.

The reaction of maleic anhydride with an alcohol is an alcoholysis reaction which results in the formation of an ester and a carboxylic acid. The reaction is also known as esterification. The reaction is relatively fast and requires no catalyst, although acid or base catalysts may be used.

The net reaction may be represented as shown below. $P_x$ and $P_y$ represent the remainder of the copolymer/terpolymer and ROH is a representative side chain precursor.

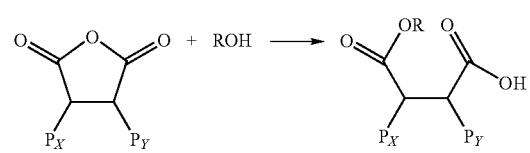

In the method two side chains precursors represented by ROH may react at the same maleic anhydride monomer to give a compound of general formula

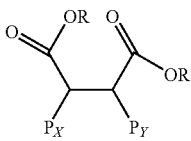

Alternatively, only one side chain precursor reacts per maleic anhydride monomer. This leaves the unit derived from maleic anhydride with a free carboxylic acid group, which may be derivatised at a later stage in the method. This group may also be deprotonated to give an ionic backbone in the polymeric material.

After reaction of the side chain precursors with a backbone precursor which comprises units derived from maleic anhydride in the backbone, any unreacted units derived from maleic anhydride in the backbone may be ring-opened. This may be performed by hydrolysis, or using a base. The resulting product may be ionisable. This further reaction step has particular utility when there is a large proportion of maleic anhydride in the backbone, for instance in an alternating copolymer.

In a preferred aspect of the invention the backbone precursors comprise pendant units of general formula (III)

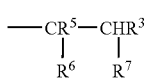
(III)

wherein $R^3$ is H or $C_{1-6}$ alkyl, $R^5$ is H or $C_{1-6}$ alkyl and $R^6$ and $R^7$ are H or an acylating group, provided at least one of $R^6$ and $R^7$ is an acylating group, or $R^6$ and $R^7$ are linked to form, together with the carbon atoms to which they are attached, a group of formula (IV):

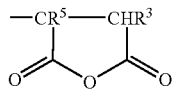
(IV)

and the side chain precursors are of general formula (V)

$$HX^1—Y—X^2H \quad (V)$$

wherein
$X^1$ is O, S or $NR^4$;
$X^2$ is selected from O, S, $(CH_2)_n$ or $NR^4$; wherein n is 1-6; and $R^4$ is H or $C_{1-6}$ alkyl; and
Y is a hydrophilic polymeric group;
and in the method, the group $HX^1$ in compound of formula (V) reacts with the units of general formula (III) or (IV) to give the amphiphilic polymeric material wherein the side chains are of general formula (I)

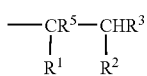
(I)

wherein $R^1$ and $R^2$ are each, independently is H, —C(O)$WR^4$ or —C(O)Q;
provided that at least one of $R^1$ and $R^2$ is the group —C(O)Q;

or and $R^2$ together form a cyclic structure together with the carbon atoms to which they are attached, of formula (II)

(II)

wherein W is O or $NR^4$;
Q is a group of formula —$X^1$—Y—$X^2$P;
T is a group of formula —N—Y—$X^2$—P; and
P is H or another backbone.

The side chains in the amphiphilic polymeric material thus comprise a unit derived from the acylating group of the backbone precursors.

The preferred substituents are the same as those given above for the preferred side chains in the polymeric material.

The composition produced according to this invention, may be used in a variety of applications, but is typically used in the manufacture of a comestible which is food-grade (i.e. edible). Typically, the amphiphilic polymeric material is produced using the method of the first aspect of the invention, and this is then added to a comestible. Preferably, the comestible is a chewing gum base or chewing gum composition. A typical chewing gum composition comprises 1-90% by weight of the amphiphilic polymeric material, preferably, 2-50%, more preferably 2-25%, most preferably 2-15% by weight. The composition produced in the first aspect of the invention may act as a substitute for part or all of the ingredients in the gum base which contribute to adhesiveness.

Alternatively, the gum base comprises no amphiphilic polymeric material. Instead, the amphiphilic material is added to a chewing gum composition independently of the chewing gum base. Most typically, the amphiphilic polymer is added to both the gum base and chewing gum composition.

The chewing gum base comprises, in addition to the amphiphilic polymeric material, conventional ingredients known in the art.

The chewing gum base may comprise 0-6% by weight wax. Examples of waxes which may be present in the gum base include microcrystalline wax, natural wax, petroleum wax, paraffin wax and mixtures thereof. Waxes normally aid in the solidification of gum bases and improving the shelf-life and texture. Waxes have also been found to soften the base mixture, improve elasticity during chewing and affect flavour retention. Preferably, the gum base comprises substantially no wax, and these properties are provided by the polymeric material. However, in some embodiments wax is present and this works with the amphiphilic polymeric material to control the release of the active.

The chewing gum base may comprise an elastomeric material which provides desirable elasticity and textural properties as well as bulk. Suitable elastomeric materials include synthetic and natural rubber. More specifically, the elastomeric material is selected from butadiene-styrene copolymers, polyisobutylene and isobutylene-isoprene copolymers. It has been found that if the total amount of elastomeric material is too low, the gum base lacks elasticity, chewing texture and cohesiveness, whereas if the content is too high, the gum base is hard and rubbery. Typical gum bases contain 10-70% by weight elastomeric material, more typically 10-15% by weight. Typically, the polymeric material will form at least 1% by weight, preferably at least 10% by weight, more preferably at least 50% by weight of the elastomeric material in the chewing gum base. In some embodiments, the polymeric material completely replaces the elastomeric material in the chewing gum base.

Elastomer plasticisers (also known as elastomer solvents) aid in softening the elastomeric material and include methyl glycerol or pentaerythritol esters of rosins or modified rosins, such as hydrogenated, dimerized, or polymerized rosins or mixtures thereof. Examples of elastomer plasticisers suitable for use in the chewing gum base include the pentaerythritol ester of partially hydrogenated wood rosin, pentaerythritol ester of wood rosin, glycerol ester of partially dimerized rosin, glycerol ester of polymerised rosin, glycerol ester of tall oil rosin, glycerol ester of wood rosin and partially hydrogenated wood rosin and partially hydrogenated methyl ester of rosin; terpene resins including polyterpene such as d-limonene polymer and polymers of α-pinene or β-pinene and mixtures thereof. Elastomer plasticisers may be used up to 30% by weight of the gum base. The preferred range of elastomer solvent, however, is 2-18% by weight. Preferably it is less than 15% by weight. Alternatively, no elastomer solvent may be used.

The weight ratio of elastomer plus polymeric material to elastomer plasticiser is preferably in the range (1 to 50):1 preferably (2 to 10):1.

The chewing gum base preferably comprises a non-toxic vinyl polymer. Such polymers may have some affinity for water and include poly(vinyl acetate), ethylene/vinyl acetate and vinyl laurate/vinyl acetate copolymers. Preferably, the non-toxic vinyl polymer is poly(vinyl acetate). Preferably, the non-toxic vinyl polymer is present at 15-45% by weight of the chewing gum base. The non-toxic vinyl polymer should have a molecular weight of at least 2000.

In alternative embodiments, the chewing gum base comprises no vinyl polymer.

The chewing gum base preferably also comprises a filler, preferably a particulate filler. Fillers are used to modify the texture of the gum base and aid in its processing. Examples of typical fillers include calcium carbonate, talc, amorphous silica and tricalcium phosphate. Preferably, the filler is silica, or calcium carbonate. The size of the filler particle has an effect on cohesiveness, density and processing characteristics of the gum base on compounding. Smaller filler particles have been shown to reduce the adhesiveness of the gum base.

The amount of filler present in the chewing gum base is typically 0-40% by weight of the chewing gum base, more typically 5-15% by weight.

Preferably, the chewing gum base comprises a softener. Softeners are used to regulate cohesiveness, to modify the texture and to introduce sharp melting transitions during chewing of a product. Softeners ensure thorough blending of the gum base. Typical examples of softeners are hydrogenated vegetable oils, lanolin, stearic acid, sodium stearate, potassium stearate and glycerine. Softeners are typically used in amounts of about 15% to about 40% by weight of the chewing gum base, and preferably in amounts of from about 20% to about 35% of the chewing gum base.

A preferred chewing gum base comprises an emulsifier. Emulsifiers aid in dispersing the immiscible components of the chewing gum composition into a single stable system. Suitable examples are lecithin, glycerol, glycerol monooleate, lactylic esters of fatty acids, lactylated fatty acid esters of glycerol and propylene glycol, mono-, di-, and tri-stearyl acetates, monoglyceride citrate, stearic acid, stearyl monoglyceridyl citrate, stearyl-2-lactylic acid, triacyetyl glycerin, triethyl citrate and polyethylene glycol. The emulsifier typically comprises from about 0% to about 15%, and preferably about 4% to about 6% of the chewing gum base.

The chewing gum base detailed above may be used to form a chewing gum composition. The chewing gum composition may comprise a gum base and one or more sweetening or flavouring agents. Typically; the chewing gum composition comprises both a sweetening and a flavouring agent. The chewing gum composition may additionally comprise other agents, including medicaments, nutraceutical actives, herbal extracts, stimulants, fragrances, sensates to provide cooling, warming or tingling actions, microencapsulates, abrasives, whitening agents and colouring agents.

Preferably, the chewing gum composition comprises a variety of other ingredients, for instance, a biologically active ingredient such as a medicament.

The biologically active ingredient is any substance which modifies a chemical or physical process in the human or animal body. Preferably, it is a pharmaceutically active ingredient and is, for instance, selected from anti-platelet aggregation drugs, erectile dysfunction drugs, decongestants, anaesthetics, oral contraceptives, cancer chemotherapeutics, psychotherapeutic agents, cardiovascular agents, NSAID's, NO Donors for angina, non-opioid analgesics, antibacterial drugs, antacids, diuretics, anti-emetics, antihistamines, anti-inflammatories, antitussives, anti-diabetic agents (for instance, insulin), opioids, hormones and combinations thereof. Preferably, the active ingredient is a stimulant such as caffeine or nicotine. Alternatively, the active ingredient is an analgesic. A further example of an active ingredient is insulin.

In one embodiment of the invention, the biologically active ingredient is a non-steroidal anti-inflammatory drug (NSAID), such as diclofenac, ketoprofen, ibuprofen or aspirin. Alternatively the active ingredient is paracetamol (which is generally not classed as an NSAID).

In a different embodiment of the invention, the biologically active ingredient is a vitamin, mineral, or other nutritional supplement.

The biologically active ingredient may be an anti-emetic, for instance Dolasetron. Alternatively the biologically active ingredient is an erectile dysfunction drug, such as sildenafil citrate.

Generally the chewing gum composition comprises 0.01-20% wt active ingredient, more typically 0.1-5 wt %. The chewing gum composition may be in unit dosage form suitable for oral administration. The unit dosage form preferably has a mass in the range 0.5-4.5 g, for instance around 1 g. Generally, the chewing gum composition comprises 1-400 mg biologically active ingredient, more typically 1-10 mg, depending on the active ingredient. When the active ingredient is nicotine, for instance, the chewing gum composition typically comprises 1-5 mg nicotine. When the active ingredient is a non-steroidal anti-inflammatory drug, such as ibuprofen, the composition typically comprises 10-100 mg active ingredient.

The amount of gum base in the final chewing gum composition is typically in the range 5-95% by weight of the final composition, with preferred amounts being in the range 10-50% by weight, more preferably 15-25% by weight.

The method of forming the chewing gum composition typically comprises blending the gum base with the sweetening and/or flavouring agents. Standard methods of production of chewing gum compositions are described in *Formulation and Production of Chewing and Bubble Gum. ISBN: 0-904725-10-3*, which includes manufacture of gums with coatings and with liquid centres.

Typically, chewing gum compositions are made by blending gum base with sweetening and/or flavouring agents in molten form, followed by cooling of the blend. Such a method may be used in the present invention.

In the laboratory, a HAAKE MiniLab Micro Compounder (Thermo Fisher Corporation) may be used to form both the gum base and the chewing gum composition.

In the case of the gum base, the ingredients are typically mixed together by adding them in stages at a temperature in the range 80-120° C., typically around 100° C. After the gum base has formed, the material is extruded out of the MiniLab.

It will be noted that the MiniLab Compounder would not be used to mix large scale batches of chewing gum. An industrial scale machine, such as a Z-blade mixer would be used in this case.

The chewing gum composition may require heating to a temperature of around 100° C. (for instance, in the range 80-120° C.) in order to uniformly mix the components. Amphiphilic polymeric material as made in the first aspect of the invention is added at either the gum base-forming step, or when the chewing gum composition is formed. Polymeric material may be added during both of these steps.

Preferably the mixture is heated to a temperature in the range 80-120° C., typically around 100° C. The mixture is generally cooled to a temperature in the range 40-80° C., preferably 50-70° C. If a biologically active ingredient is to be included in the composition, it is generally added at this stage.

After the mixing is complete, the chewing gum composition may be extruded.

During any of the steps of the method, the mixture may be stirred to improve homogeneity.

The final stage may comprise use of compression to form the chewing gum composition which may be, for instance, a compressed chewing gum formulation.

A unit dosage form of the chewing gum composition may be formed by extruding the chewing gum and shaping the extrudate to the desired form. The unit dosage form typically has a mass in the range 0.5-2.5 g, typically around 1 g. The dosage unit may take the form of a cylindrical or spherical body, or a tab.

Typically, the chewing gum composition comprises 5-95% by weight, preferably 10-50% by weight, more preferably 15-45% of the chewing gum base. Additional polymeric material may also be added to form the chewing gum composition, in an amount such that it comprises 1-15%, more preferably 3-15% of the chewing gum composition.

The steps to form the chewing gum composition may be carried out sequentially in the same apparatus, or may be carried out in different locations, in which case there may be intermittent cooling and heating steps.

Figure 2:
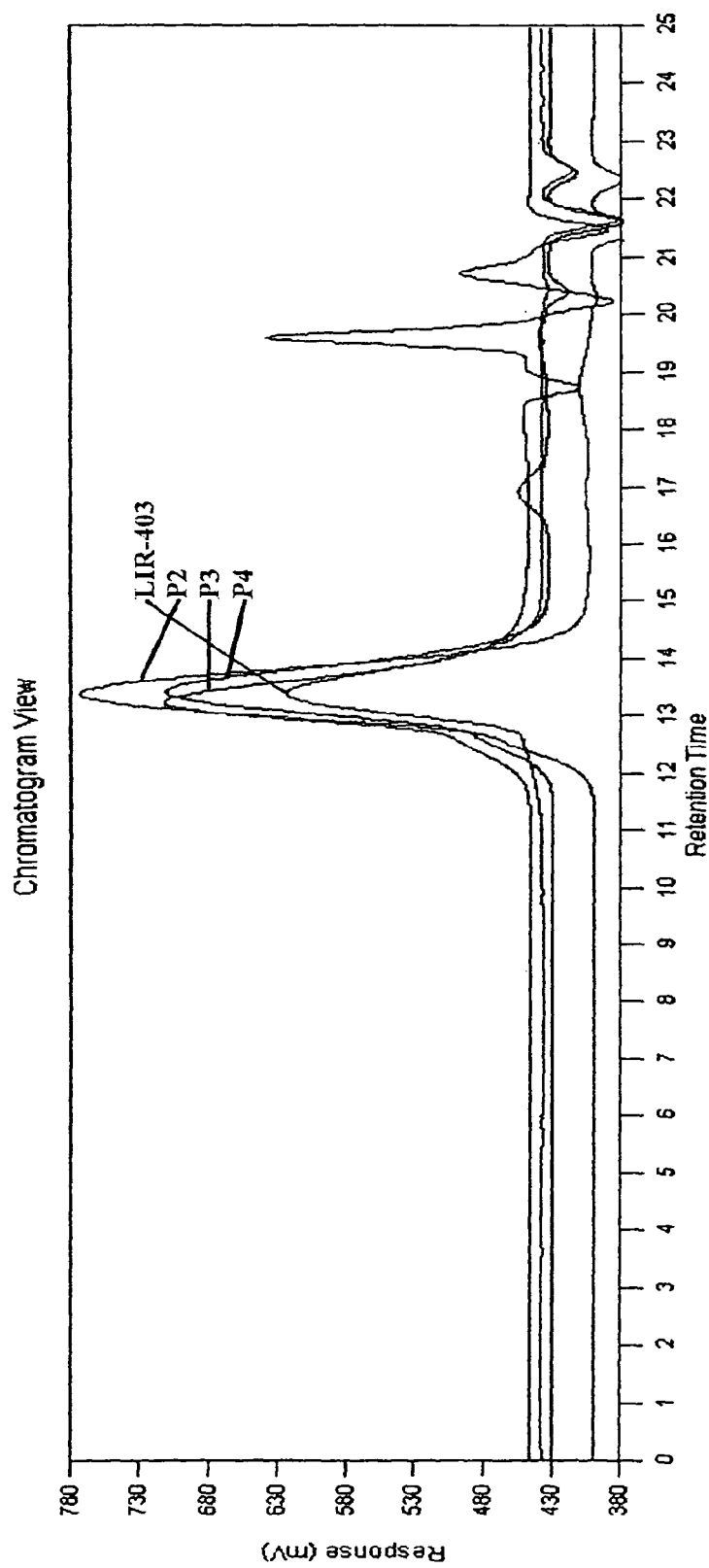
Figure 3:
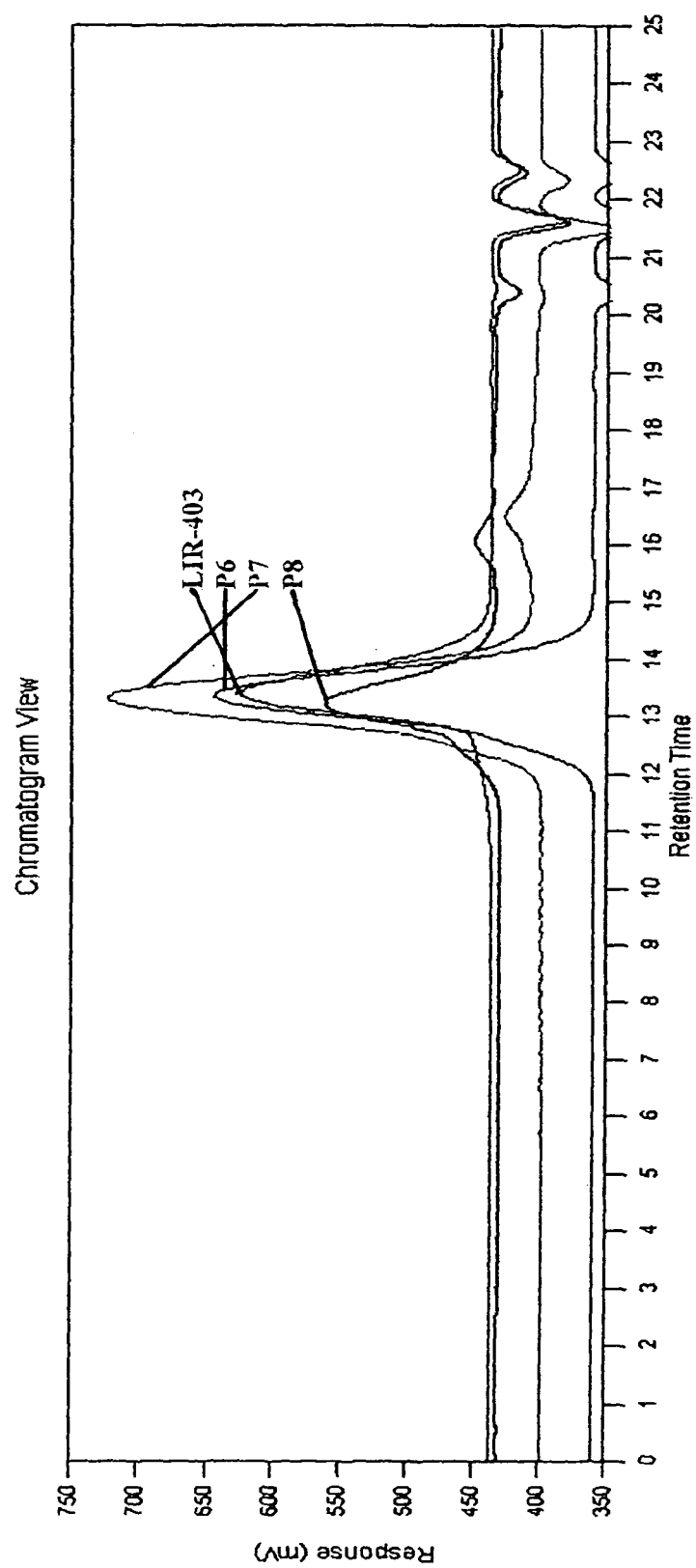
Figure 4:
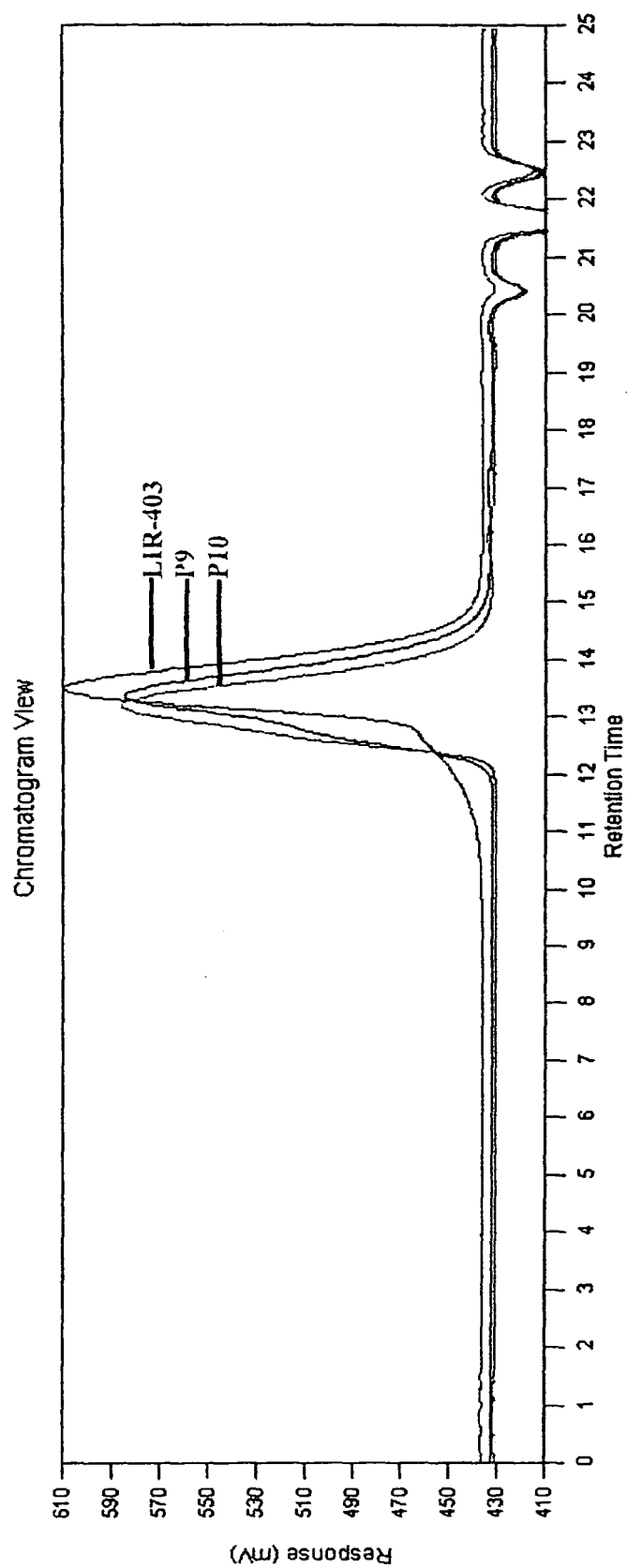
Figure 5:
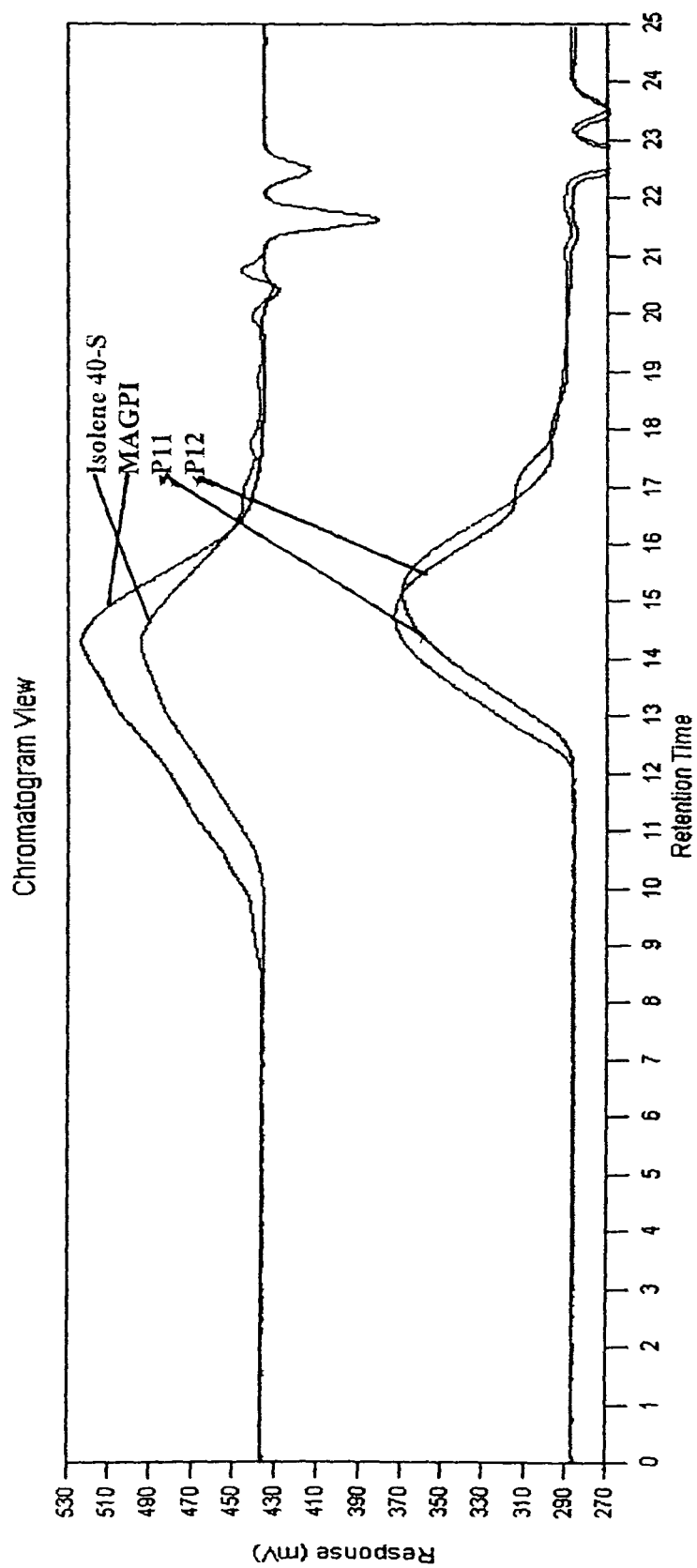
Figure 6:
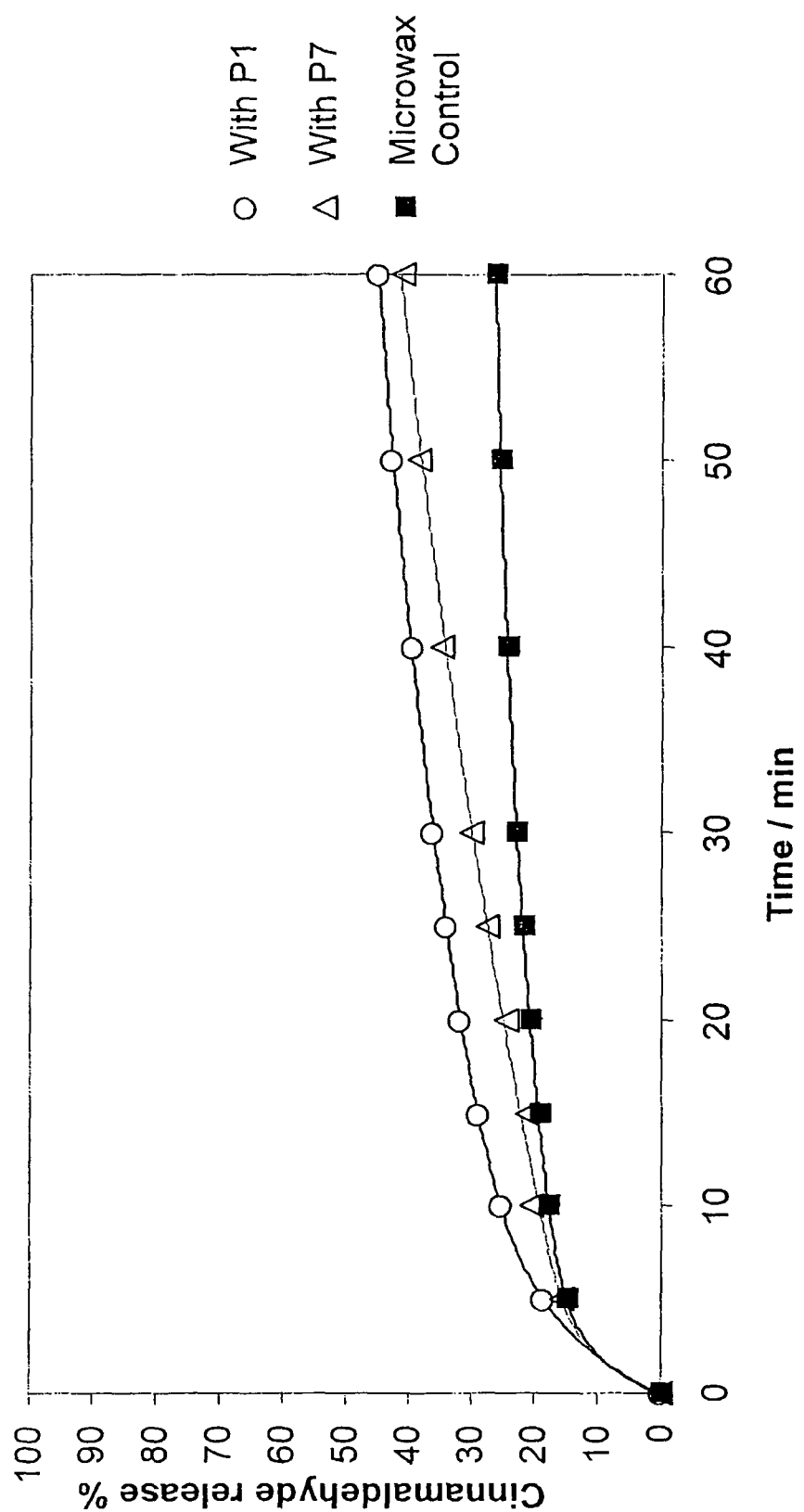

The invention will now be illustrated further in the following Examples, and with reference to the accompanying drawings, in which:

FIG. 1 compares the molecular weight distribution of a number of batches of P1 as determined by GPC;

FIG. 2 compares the molecular weight distribution of samples of the graft copolymers $P2_a$, $P3_c$, and P4 with the LIR-403 backbone starting material as determined by GPC;

FIG. 3 compares the molecular weight distribution of samples of the graft copolymers P6, P7, and P8 with the LIR-403 backbone starting material as determined by GPC;

FIG. 4 compares the molecular weight distribution of samples of the graft copolymers P9, and P10 with the LIR-410 backbone starting material as determined by GPC;

FIG. 5 compares the molecular weight distribution of samples of the graft copolymers P11, and P12 with the Isolene 40-S and MAGPI polyisoprene backbone starting materials as determined by GPC; and FIG. 6 compares cumulative cinnamaldehyde release in artificial saliva from gum containing P1, P7, and a control gum determined using HPLC.

MATERIALS

Two different forms of PIP-g-MA have been used; the first supplied under the name LIR-403 by Kuraray and the other is a PIP-g-MA synthesized by the reaction of maleic anhydride with polyisoprene (Isolene 40-S) in 1,2-dichlorobenzene (See Example 17). This latter material will subsequently be referred to as maleic anhydride-grafted-polyisoprene (MAGPI) to avoid confusion with PIP-g-MA. The polyisoprene used in the synthesis of MAGPI, Isolene 40-S manufactured by Royal Elastomers, is a synthetic polyisoprene with a glass transition temperature of −65° C., a typical molecular weight of 32,000, and a relatively broad molecular weight distribution compared with that of LIR-403. Subsequently the resulting MAGPI has a similarly broader molecular weight distribution compared to LIR-403.

Reference Example A

Determination of Molecular Weights of Polymeric Materials and Free MPEG

The polymer samples were analyzed using a PL-GPC50plus GPC system manufactured by Polymer Labs. The following conditions were used:
Eluent: THF stabilised with 250 ppm BHT
Eluent RI: 1.408
Flow Rate (ml/min): 1
Temperature: 40° C.
Column Set Name: 2 Columns 30 mm PL gel 5 um MIXED-D
Detector Name: DRI
Detector Calibration Curve: Polystyrene Standards (538 Da-265000 Da)

This apparatus was used to determine the molecular weights of all of the graft copolymers. In order to determine the amount of free MPEG present in the samples, 10 different solutions of known concentration of MPEG 2000 in THF (0.05-2 mg/mL) were accurately prepared and analysed on the apparatus. The relevant intensity of the samples was then used to generate a calibration curve which was used to generate the concentration of free MPEG in the samples.

Reference Example B

Determination of Degrees of Grafting with PEG Using FT-IR

The analysis described below is used to calculate the degree of grafting of side chain precursor to backbone precursor. The analysis determines the amount of cyclic units derived from maleic anhydride in the backbone precursor starting material and product polymeric material. The degree of grafting calculation is based on the assumption that all units derived from maleic anhydride react with side chain precursors.

The analysis was carried out on a PerkinElmer Paragon 2000 Infrared spectrometer. Samples for analysis were dissolved in spectrometric grade chloroform and placed in a liquid cell (Barium fluoride plates separated by PTFE spacer) in a mounting bracket/carriage in an IR beam with known cell path length.

A sample of the batch of PIP-g-MA used to synthesize the graft copolymer was accurately weighed out (~0.1 g (+/−0.05 g)) into the stoppered conical flask and dissolved in 10 g of accurately weighed out chloroform. The FT-IR of the sample was collected, and the percentage transmission values measured at 1830 cm$^{-1}$ and at 1790 cm$^{-1}$ recorded. The sample of polymer was accurately weighed out (~1.5 g (+/−0.5 g)) into the stoppered conical flask, dissolved in 10 g of accurately weighed out chloroform, and studied by FT-IR in a similar manner. The concentration of maleic anhydride in each sample was then calculated using the following formula:

$$\mu \text{mole/g (in sample)} = \frac{33600}{C} \times \frac{\text{Log}_{10}\% \ T (\text{at } 1830.0 \ \text{cm}^{-1})}{\% \ T (\text{at } 1790.0 \ \text{cm}^{-1})}$$

where C is the concentration in the test solution (quoted in mg g$^{-1}$). The percentage conversion of maleic anhydride can then be determined by comparing the values from the backbone and graft copolymer.

This method can also be used to determine the degrees of grafting in the other polymeric materials (P2-P8).

Reference Example C

Cinnamaldehyde Release Tests on Chewing Gums—Experimental Method

Each pre-shaped piece of gum was weighed before chewing, and the weight recorded to allow estimation of the total quantity of drug in each piece.

A 'ERWEKA DRT-1' chewing apparatus from AB FIA was used, which operates by alternately compressing and twisting the gum in between two mesh grids. A water jacket, with the water temperature set to 37° C. was used to regulate the temperature in the mastication cell to that expected when chewed in vivo, and the chew rate was set to 40 'chews' per minute. The jaw gap was set to 1.6 mm.

40 mL artificial saliva (composed of an aqueous solution of various salts, at approx pH 6—see below, Table 2) was added to the mastication cell, then a plastic mesh placed at its bottom. A piece of gum of known weight was placed on the centre of the mesh, and a second piece of mesh put on top.
Artificial Saliva:

TABLE 2

Artificial Saliva Formulation

| Components | Quantity (mmol/L) |
|---|---|
| KH$_2$PO$_4$ | 2.5 |
| Na$_2$HPO$_4$ | 2.4 |
| KHCO$_3$ | 15 |
| NaCl | 10 |
| MgCl$_2$ | 1.5 |
| CaCl$_2$ | 1.5 |
| Citric acid | 0.15 |

PH adjusted to 6.7 with HCl

Procedure for Analysing the Release Profiles of Active Ingredients from Gum

The parameters in Table 3 were always used in chewing unless otherwise noted.

TABLE 3

Chewing Parameters

| Parameter | Value |
|---|---|
| Temperature | 37° C. |
| Gaps between jaws | 1.6 mm |
| Twisting angle | 20° |
| Chew Frequency | 40 strokes/min |

At the start of each run, the cell containing the artificial saliva and gum was left for 5 minutes so that the system could equilibrate to 37° C. The gum was then masticated. A sample volume of 0.5 mL was then withdrawn from the test cell periodically during a release run (5, 10, 15, 20, 25, 30, 40, 50 and 60 minutes).

All the samples were then analysed by HPLC using a typical Perkin Elmer HPLC Series 200 system, equipped with an autosampler, pump, and diode array detector. Data handling and instrument control was provided via Totalchrom v 6.2 software. The columns and mobile phase were adjusted to the active ingredient as follows:

Cinnamaldehyde details: Column—Varian Polaris 5u C18-A 250×4.6 m. Mobile Phase—Acetonitrile/0.05% orthophosphoric acid (60/40). Flow rate—1 mL/min. Detection—UV 250 nm. Inj vol—5 uL Two injections into the HPLC column were used for each sample, to ensure reproducibility.

Example 1

Reaction of polyisoprene-graft-maleic anhydride with poly(ethylene glycol)methyl ether (Preparation of P1$_a$) in a Reaction Flask PIP-g-MA (300 g, Polyisoprene-graft-maleic anhydride obtained from Kuraray, LIR-403 grade) having the CAS No. 139948-75-7, an average M$_w$ of approximately 25,000 and a typical level of grafting of MA of around 1.0 mol %, and poly(ethylene glycol)methyl ether (PEGME) (212 g, purchased from Clariant), having an average molecular weight of 2000 were weighed out and added to a reaction flask with a 1 L capacity, equipped with an overhead stirrer. The PIP-g-MA was present as a liquid, and PEGME as a solid. A flow of nitrogen gas was passed through the vessel, which was then heated to 120° C. using an oil bath. Stirring of the molten mixture then commenced and the vessel was then heated to 160° C. An essentially homogeneous mixture was formed, with the backbone precursors dissolved in the side chain precursors.

The reaction mixture was maintained at this temperature for a total of approximately 24 hours. Following this it was allowed to cool to below 100° C. and water (400 mL) was then added. The mixture was allowed to cool to room temperature and the water was removed by filtration, following which the product was dried under vacuum at 40-50° C.

The product was studied using GPC and FTIR. A comparison of the GPC chromatogram of this and other samples of P1 may be found in FIG. 1.

Example 2

Reaction of polyisoprene-graft-maleic anhydride with polyethylene glycol)methyl ether (Preparation of P1$_b$) in a Batch Ploughshare Mixer PIP-g-MA (738 g, Polyisoprene-graft-maleic anhydride obtained from Kuraray, LIR-403 grade) having the CAS No. 139948-75-7, an average M$_w$ of approximately 25,000 and a typical level of grafting of MA of around 1.0 mol %, and poly(ethylene glycol)methyl ether (PEGME) (526 g, purchased from Clariant), having an average molecular weight of 2000 were weighed out and added to a Lodige 3 L batch ploughshare mixer, equipped with an overhead stirrer. A flow of nitrogen gas was passed through the vessel, which was then heated to 120° C. using an oil bath. Stirring of the molten mixture then commenced and the vessel was then heated to 160° C.

The reaction mixture was maintained at this temperature for a total of approximately 24 hours. Following this it was allowed to cool to below 100° C. and water (1 L) was then added. The mixture was allowed to cool to room temperature and the water was removed by filtration, following which the product was dried under vacuum at 40-50° C.

The product was studied using GPC and FTIR. A comparison of the GPC chromatogram of this and other samples of P1 may be found in FIG. 1.

Example 3

Reaction of polyisoprene-graft-maleic anhydride with poly(ethylene glycol)methyl ether (Preparation of P1$_c$) in a Z-Blade Mixer PIP-g-MA (385 g, Polyisoprene-graft-maleic anhydride obtained from Kuraray, LIR-403 grade) having the CAS No. 139948-75-7, an average M$_w$ of approximately 25,000 and a typical level of grafting of MA of around 1.0 mol %, and poly(ethylene glycol)methyl ether (PEGME) (293 g, purchased from Clariant), having an average molecular weight of 2000 were weighed out and added to a Winkworth Z-blade mixer, equipped with an overhead stirrer. A flow of nitrogen gas was passed through the vessel, which was then heated to 120° C. using an oil bath. Stirring of the molten mixture then commenced and the vessel was then heated to 160° C.

The reaction mixture was maintained at this temperature for a total of approximately 24 hours. Following this it was allowed to cool to below 100° C. and water (0.5 L) was then added. The mixture was allowed to cool to room temperature and the water was removed by filtration, following which the product was dried under vacuum at 40-50° C.

The product was studied using GPC and FTIR. A comparison of the GPC chromatogram of this and other samples of P1 may be found in FIG. 1.

Example 4

Reaction of polyisoprene-graft-maleic anhydride with poly(ethylene glycol)methyl ether in Toluene Solvent (Preparation of P1$_d$) [Comparative]

PIP-g-MA (5.25 Kg, Polyisoprene-graft-maleic anhydride obtained from Kuraray, LIR-403 grade) having the CAS No. 139948-75-7, an average M$_w$ of approximately 25,000 and a typical level of grafting of MA of around 1.0 mol %, and poly(ethylene glycol)methyl ether (PEGME) (4.00 kg, purchased from Aldrich), having an average molecular weight of 2000 were weighed out and added to an air-tight jacketed reactor with a twenty liter capacity, equipped with an overhead stirrer. Toluene (10.0 kg) was added to the reactor to dissolve the starting materials, and a flow of nitrogen gas passed through the vessel.

The vessel was then heated to reflux the toluene (115-116° C.) using an oil bath set to 140° C. connected to the reactors jacket. A Dean-Stark trap and condenser between the vessel and nitrogen outlet were used in order to remove any water from the poly(ethylene glycol)methyl ether and toluene by means of azeotropic distillation. Thus water was collected in the Dean-Stark trap over the course of the reaction.

The reaction mixture was refluxed for a total of approximately 24 hours. The reaction can also be catalysed by addition of acid or base. The product was purified in 2 L batches by adding the still warm (50° C.) material to 3 L tanks of deionised water. In the case of each batch the water was removed by filtration and the process of washing the graft copolymer with deionised water, and removing the water wash with the aid of filtration repeated a further five times. The product was dried under vacuum at 50° C. overnight.

The product was studied using GPC and FTIR. A comparison of the GPC chromatogram of this and other samples of P1 may be found in FIG. 1.

Example 5

Reaction of polyisoprene-graft-maleic anhydride with Jeffamine M-1000 (Preparation of P2$_a$) with a 1:1 Ratio of Graft to each maleic anhydride Group PIP-g-MA (150.0 g, Polyisoprene-graft-maleic anhydride obtained from Kuraray, LIR-403 grade) having the CAS No. 139948-75-7, an average M$_w$ of approximately 25,000 and a typical level of grafting of MA of around 1.0 mol %, and Jeffamine M-1000 (21.8 g, obtained from Huntsman), having an average molecular weight of 1000 were added to a reaction flask with a 250 mL capacity, equipped with an overhead stirrer. A flow of nitrogen gas was passed through the vessel, which was then heated to 120° C. using an oil bath. Stirring of the molten mixture then commenced and the vessel was then heated to 160° C.

The reaction mixture was maintained at this temperature for a total of approximately 24 hours. Following this it was allowed to cool to approximately 80° C. and water (200 mL) was then added. The mixture was allowed to cool to room temperature and the water was removed by decantation, following which the product was dried under vacuum at 40-50° C.

The structure was confirmed using GPC and FTIR.

Example 6

Reaction of polyisoprene-graft-maleic anhydride with Jeffamine M-1000 (Preparation of P2$_b$), with a 1:1 Ratio of Graft to each maleic anhydride Group This product was prepared using the same methodology as Example 5 using LIR-403 (500 g) of Jeffamine M-1000 (72.7 g), and a 1 L reaction flask. It was not necessary to add water to the product due to the efficiency of the reaction between the polymeric backbones and this graft determined from the previous experiment. The structure was confirmed using GPC and FTIR.

Example 7

Reaction of polyisoprene-graft-maleic anhydride with Jeffamine M-1000 (Preparation of P3$_a$) with a 2:1 Ratio of Graft to each maleic anhydride Group This product was prepared using the same methodology as Example 5 using 43.6 g of Jeffamine M-1000.

The structure was confirmed using GPC and FTIR.

Example 8

Reaction of polyisoprene-Graft-maleic anhydride with Jeffamine M-1000 (Preparation of P3$_b$) with a 2:1 Ratio of Graft to each maleic anhydride Group using an Organic Solvent [Comparative]

This material was prepared using the same methodology as Example 7 but used toluene as a solvent.

PIP-g-MA (150.0 g, Polyisoprene-graft-maleic anhydride obtained from Kuraray, LIR-403 grade) having the CAS No.

139948-75-7, an average $M_w$ of approximately 25,000 and a typical level of grafting of MA of around 1.0 mol %, and Jeffamine M-1000 (21.8 g, obtained from Huntsman), having an average molecular weight of 1000 were added to a reaction flask with a 250 mL capacity, equipped with an overhead stirrer. A flow of nitrogen gas was passed through the vessel, which was then heated to 120° C. using an oil bath. Toluene (195.0 g) was added to the reactor to dissolve the starting materials, and a flow of nitrogen gas passed through the vessel.

The vessel was then heated to reflux the toluene in an oil bath set to 170° C. connected to the reactors jacket. A Dean-Stark trap and condenser between the vessel and nitrogen outlet were used in order to remove any water from the poly (ethylene glycol)methyl ether and toluene by means of azeotropic distillation. Thus water was collected in the Dean-Stark trap over the course of the reaction.

The reaction mixture was maintained at this temperature for a total of approximately 24 hours. Following this it was allowed to cool to approximately 80° C. and precipitated in water (2 L). The stirred mixture was allowed to cool for 30 min, after which the water was removed by decantation, and the product was dried under vacuum at 40-50° C.

The structure was confirmed using GPC and FTIR.

Example 9

Reaction of polyisoprene-graft-maleic anhydride with Jeffamine M-1000 (Preparation of P3$_c$) with a 2:1 Ratio of Graft to each maleic anhydride Group This product was prepared using the same methodology as Example 6 using LIR-403 (500 g) and Jeffamine M-1000 (43.6 g), and a 1 L reaction flask. The structure was confirmed using GPC and FTIR.

Example 10

Reaction of polyisoprene-graft-maleic anhydride with Jeffamine M-1000 (Preparation of P4) with a 2.8:1 Ratio of Graft to each maleic anhydride Group This product was prepared using the same methodology as Example 6 using LIR-403 (62.3 g) and Jeffamine M-1000 (25.3 g), and a 250 mL reaction flask. The structure was confirmed using GPC and FTIR.

Example 11

Reaction of polyisoprene-graft-maleic anhydride with Jeffamine M-2070 (Preparation of P5) with a 0.5:1 Ratio of Graft to each maleic anhydride Group This product was prepared using the same methodology as Example 6 using LIR-403 (500 g) and Jeffamine M-2070 (72.7 g), and a 1 L reaction flask. The structure was confirmed using GPC and FTIR.

Example 12

Reaction of polyisoprene-graft-maleic anhydride with Jeffamine M-2070 (Preparation of P6) with a 1:1 Ratio of Graft to each maleic anhydride Group This product was prepared using the same methodology as Example 6 using LIR-403 (500 g) and Jeffamine M-2070 (145.0 g), and a 1 L reaction flask. The structure was confirmed using GPC and FTIR.

Example 13

Reaction of polyisoprene-graft-maleic anhydride with Jeffamine M-2070 (Preparation of P7) with a 2:1 Ratio of Graft to each maleic anhydride Group This product was prepared using the same methodology as Example 6 using LIR-403 (500 g) and Jeffamine M-2070 (290.0 g), and a 1 L reaction flask. The structure was confirmed using GPC and FTIR.

Example 14

Reaction of polyisoprene-graft-maleic anhydride with Jeffamine M-2070 (Preparation of P8) with a 2.8:1 Ratio of Graft to each maleic anhydride Group This product was prepared using the same methodology as Example 6 using LIR-403 (61.8 g) and Jeffamine M-2070 (50.18 g), and a 250 mL reaction flask. The structure was confirmed using GPC and FTIR.

Example 15

Reaction of polyisoprene-Graft-maleic acid monomethyl ester with Jeffamine M-1000 (Preparation of P9) with a 1:1 Ratio of Graft to each maleic acid mono ester Group This product was prepared using the same methodology as Example 6 using LIR-410 (60 g) and Jeffamine M-1000 (24.5 g), and a 250 mL reaction flask. The structure was confirmed using GPC and FTIR.

Example 16

Reaction of polyisoprene-graft-maleic acid monomethyl ester with Jeffamine M-2070 (Preparation of P10) with a 1:1 Ratio of Graft to each maleic acid mono ester group This product was prepared using the same methodology as Example 6 using LIR-410 (60 g) of Jeffamine M-2070 (50.0 g), and a 250 mL reaction flask. The structure was confirmed using GPC and FTIR.

Example 17

Synthesis of maleic anhydride grafted polyisoprene (MAGPI)

Polyisoprene (Isolene 40S, supplied by Royal Elastomers, 72 g), maleic anhydride (1.0 g), and 1,2-dichlorobenzene were weighed out into a 3 neck round bottom flask. The reaction flask was equipped with an overhead stirrer, and condenser and was thoroughly purged with nitrogen gas. Stirring of the reaction mixture then commenced, and was rapidly heated up under a still nitrogen atmosphere. The reaction mixture was refluxed for five hours (180° C.). After this period the solvent from the reaction mixture was distilled off (under vacuum), and the remaining material allowed to cool to room temperature. This was then washed with acetone (3×100 mL) in-order to remove any un-reacted MA. The product was then dried under vacuum at 100° C.

To avoid confusion with the generic term polyisoprene-graft-maleic anhydride (PIP-g-MA) the products of these reactions will be referred to as MAGPI.

Example 18

Reaction of MAGPI with Jeffamine M-1000 (Preparation of P11) with a 2:1 Ratio of Graft to each maleic anhydride Group This product was prepared using the same methodology as Example 6 using MAGPI (60 g) and Jeffamine M-1000 (27.9 g), and a 250 mL reaction flask. The structure was confirmed using GPC and FTIR.

Example 19

Reaction of MAGPI with Jeffamine M-2070 (Preparation of P12) with a 2:1 Ratio of Graft to each maleic anhydride Group This product was prepared using the same methodology as Example 6 using MAGPI (60 g) and Jeffamine M-2070 (55.8 g), and a 250 mL reaction flask. The structure was confirmed using GPC and FTIR.

Example 20

Preparation of Gum Base and Chewing Gum

Chemicals

Calcium carbonate ($CaCO_3$), ester gum, hydrogenated vegetable oil (HVO), polyisobutylene (PIB), poly(vinyl acetate) (PVAc), glyceromonostearate (GMS), microwax, sorbitol liquid, sorbitol solid, and peppermint oil, were all food grade materials obtained from the Gum Base Company. Cinnamaldehyde (98+%) was obtained from Fisher-Scientific UK.

Mixing of the Chewing Gum and Chewing Gum Base:

The chewing gum base had the composition as shown in the table below:

TABLE 4

Recipe for the Manufacture of the Gum Bases

| Stage | Component | % Composition | Mass/g |
|---|---|---|---|
| 1 | PIB | 13 | 1.04 |
|   | PVAc | 6 | 0.48 |
|   | $CaCO_3$ | 6 | 0.48 |
|   | Ester Gum | 3.6 | 0.288 |
| 2 | Ester Gum | 5.4 | 0.432 |
|   | $CaCO_3$ | 9 | 0.72 |
| 3 | PVAc | 9 | 0.72 |
|   | Ester Gum | 9 | 0.72 |
|   | $CaCO_3$ | 15 | 1.2 |
| 4 | HVO | 12 | 0.96 |
|   | GMS | 6 | 0.48 |
|   | X | 6 | 0.48 |
|   | Total | 100 | 8 |

X is either microcrystalline wax in the case of the S3 control, P1 or P7. HVO=hydrogenated vegetable oil, PVAc=poly(vinyl acetate).

The gum base materials were mixed on a Haake Minilab micro compounder manufactured by the Thermo Electron Corporation, which is a small scale laboratory mixer/extruder. The screws were set to co-rotate at 80 turns/min.

The ingredients were mixed together in four steps, the gum only being extruded after the final step. The gum base was mixed at 100° C.

The chewing gum was mixed according to the following table.

TABLE 5

Ingredients for the Chewing Gum

| Stage | Time | Component | Amount |
|---|---|---|---|
| 1 | 15 min | 37.5% Gum Base Containing X | 3 g |
|   |   | 10% Sorbitol Liquid | 0.8 g |
|   |   | 17% Sorbitol Powder | 1.36 g |
| 2 | 15 min | 25.5% Sorbitol Powder | 2.04 g |
|   |   | 6% X | 0.48 g |
|   |   | 3% Sorbitol Liquid | 0.24 g |
|   |   | 1% Cinnamaldehyde Flavour | 0.08 mL |
|   | 30 min | TOTAL | 8 g |

X is either P1, or P7 or, microcrystalline wax in the case of the S3 control.

The gum was mixed using the same equipment as the base and extruded after the final step. The gum was mixed at 60° C. In stage 1 the sorbitol liquid and powder were premixed prior to adding them to the gum.

The gums were tested using the method described in Reference Example C. The fastest and highest release profile was observed for the formulation containing P1. The release rate from the P7 gum formulations was comparatively slow compared with those from P1 during the period between the $5^{th}$ and $20^{th}$ minutes. It subsequently increased to a level above that of P1, so that the total percentage amount of cinnamaldehyde released from the P7 and P1 gums was almost identical by the end of the experiment. The microwax control by contrast to the formulations containing the two polymers, has a consistently lower release rate after 5 minutes; the total amount of cinnamaldehyde released at the end of the experiment is approximately half that of the other two formulations.

A series of gum formulations were made on a laboratory compounder using either P1, P7 or in the case of the control, microwax. The P1 was $P1_d$, i.e. prepared in accordance with Example 4, but any of $P1_a$-$P1_c$ would also have been suitable, as these materials are all very similar (see FIG. 1). The finished gum samples were masticated in artificial saliva and the release of cinnamaldehyde, added as a flavour, monitored via HPLC (FIG. 6). The slowest release was observed with the microwax control. The fastest release was observed from the gum containing P1, with the formulation containing P7 observed to have only a slightly slower release profile. Thus this indicates that P7 may be a suitable component for chewing gum.

Example 21

Quantification of the levels of Toluene in Polymeric Material Synthesised without the Use of Solvent Analysis for toluene as well as tetrahydrofuran (THF), and cyclohexane was carried out on a HP 6890/5973 MSD Gas Chromatograph with Mass Selective Detector (LIMS 1066) with Headspace Sampler (Turbomatrix 40 (LIMS 1780)). Four different batches of polymer synthesised using the method described in Example 3 were tested.

GCMS Conditions:
 Column: 30 m×0.32 mm ID DB-624, df 1.8 µm
 Oven Temp: 40° C. for 20 min.
 Carrier Gas: Helium at 2.1 mL/min (Constant pressure)
 Injection Mode: Split (Split Ratio 5:1)
 Injector Temp: 140° C.

Detector: MSD ACQ Mode
(Group 1 THF SIM 42 and 72 ions; Cyclohexane SIM 56 and 84 ions)
(Group 2 (6.5 mins) Toluene SIM 65 and 91 ions)
Solvent Delay: 3 min
Transfer Line Temp: 250° C.
MS Source Temp: 230° C.
MS Quad Temp: 150° C.
Headspace Conditions:
Sample oven temp: 105° C.
Needle temp: 140° C.
Transfer temp: 140° C.
GC cycle time: 25 min
Thermostat time: 30 min
Pressure time: 0.5 min
Pressure: 25 psi
Inject time: 0.05 min
Withdrawal time: 0.5 min
Mode: Constant
Standard Preparation:
Tetrahydrofuran (THF), cyclohexane and toluene standards were used to prepare a mixed standard solution:
Approximately 0.1 g of Cyclohexane, THF and Toluene was accurately weighed, in duplicate, and into separate flasks, into a 100 mL volumetric flask and made up to the mark with Octan-1-ol, giving stock solutions 1 and 2 of Cyclohexane, THF and Toluene.
1.0 mL of each individual stock solution was pipetted, in duplicate using stock standards 1 and 2, into 100 mL Octan-1-ol to give 2 mixed standard solutions containing equivalent to approximately 10 mg/kg THF, Cyclohexane and Toluene in solution.
Further dilutions were performed as below to give Standard solutions 1A (2 mg/kg in solution), 1B (1 mg/kg in solution), 1C (0.2 mg/kg in solution) and 2A (2 mg/kg in solution check standard).
Blank Sample Preparation:
In duplicate, ~0.5000 g of each sample was weighed accurately into a headspace vial. 5 mL Octan-1-ol was added to each vial.
Spiked Sample Preparation:
In duplicate, ~0.5000 g of each sample was weighed accurately into a headspace vial. 2.5 mL Octan-1-ol and 2.5 mL mixed standard solution was added to each vial.
Analysis of Polymeric Material Produced without the Aid of Solvent:
All sample analysis was carried out in duplicate, with spiking experiments being performed on only one sample for comparison at levels of 1, 5 and 10 mg/kg for THF, Cyclohexane and Toluene. No spike recoveries were calculated as each sample blank showed significantly less than half the peak height of each analyte and therefore this was not considered necessary. The 1-octanol used as solvent contained a minor impurity eluting at the same retention time as cyclohexane. However no addition to this signal was observed in any of the sample solutions. Standard additions of approximately 1, 5 and 10 mg/kg were all readily detected.

Example 22

Quantification of the Levels of Toluene in Polymeric Material Synthesised in Toluene Solution The analysis of samples produced using the aid of solvent (Example 4) were carried out via a slightly different methodology to those in Example 21:
1) The samples were analysed by SPME headspace GCMS (SIM mode) after dissolution in methanol at 60° C. in sealed headspace vials.
2) Quantification was made by comparison of the samples with and without toluene spiked in at known levels, and analysed using a methodology similar to that used to analyse the polymers synthesized without solvent.

Summary of Results

In these results, the terms "graft" and "side chain precursor" are used interchangeably. The properties of the samples obtained from this no-solvent process using several different scales and pieces of equipment were compared, both with each other and a sample synthesised in toluene using the process outlined previously in WO 2006/016179. The polymer samples were analysed using gel permeation chromatography (Table 6).

TABLE 6

Physical Characteristics of Batches of P1 synthesised via the Methods described in Examples 1-4

| P1 Batch | $M_n$ | PDI | % Free MPEG |
|---|---|---|---|
| 1 | 31280 | 1.18 | 28.36 |
| 2 | 31710 | 1.26 | 28.06 |
| 3 | 32330 | 1.20 | 31.04 |
| 4 | 30400 | 1.14 | 28.02 |

Both the molecular weight distribution and the quantity of free MPEG in the samples were measured using GPC. FIG. 1 compares the GPC traces from the four different batches of P1. From visual comparison of the traces, and analysis of the data in Table 6 it is clear that the molecular weights and molecular weight distributions of the polymers were generally very similar from the different routes, including that from the solvent route. The levels of free MPEG were also similar. Free MPEG had a retention time around 16 minutes. The polymers were also analysed further using FT-IR and the method described in Reference Example B (Table 7).

TABLE 7

Conversion of MA into PEG ester determined by IR for Batches of P1 synthesised via the Methods Described in Examples 1-4.

| P1 Batch | (MA)μM | % MA Remaining | % Conversion |
|---|---|---|---|
| 1 | 6.47 | 8.36 | 91.64 |
| 2 | 10.20 | 12.62 | 87.38 |
| 3 | 6.23 | 8.32 | 91.68 |
| 4 | 5.09 | 6.30 | 93.70 |

Concentration of residual MA in the composition is expressed in μM/g, together with the calculated values for percentage of the original MA in the reaction mixture left in the composition, and thus conversion of MA into PEG ester (i.e. hydrophilic graft).

By observing the conversion of maleic anhydride groups to the maleic anhydride esters of the product P1 we can get a value for the degree of conversion of the maleic anhydride and thus grafting in the polymers. As will be clear from Table 7 the samples are observed to have similar conversions, i.e. approximately 90% of the maleic anhydride groups have reacted to form a monomethyl ester with the PEG. These values are calculated from spectra obtained of aliquots of the batches just prior to the addition of water.

A sample of $P1_d$ synthesized using the method described in Example 4 was determined to have 10 ppm toluene using headspace GCMS. In a similar experiment in which the PIP-g-MA was replaced with PIP-g-MaMme the resulting polymeric composition was determined to have 166 ppm of toluene. By contrast none of the samples synthesised using the no-solvent process analysed were found to have traces of toluene, cyclohexane or tetrahydrofuran, the levels being below the limit of detection (1 mg/kg, i.e. 1 ppm).

Table 8 lists a number of polymers synthesised from PIP-g-MA or PIP-g-MaMme and Jeffamine M-1000 and M-2070.

TABLE 8

Properties of Graft Copolymers Synthesized from Jeffamines.

| Polymer | Backbone | Graft | Ratio of Graft to Functional group | Mn (g mol−1) | PDI |
|---|---|---|---|---|---|
| P2$_a$ | LIR-403 | M1000 | 1 to 1 | 24600 | 1.18 |
| P3$_c$ | LIR-403 | M1000 | 2 to 1 | 23200 | 1.16 |
| P4 | LIR-403 | M1000 | 2.8 to 1 | 22400 | 1.16 |
| P5 | LIR-403 | M2070 | 0.5 to 1 | 21710 | 1.19 |
| P6 | LIR-403 | M2070 | 1 to 1 | 23850 | 1.16 |
| P7 | LIR-403 | M2070 | 2 to 1 | 25120 | 1.15 |
| P8 | LIR-403 | M2070 | 2.8 to 1 | 31340 | 1.19 |
| P9 | LIR-410 | M1000 | 1 to 1 | 22750 | 1.20 |
| P10 | LIR-410 | M2070 | 1 to 1 | 25930 | 1.16 |
| P11 | MAGPI | M1000 | 2 to 1 | 13630 | 1.77 |
| P12 | MAGPI | M2070 | 2 to 1 | 19530 | 1.67 |

M$_n$ = Number Average Molecular Weight, PDI = Polydispersity Index; both determined by GPC.

The ratio of graft to maleic anhydride can easily be varied to achieve different loadings of the graft on the backbone and thus different properties in the resulting hydrophilic material. Polymers with a higher degree of grafting will tend to be more hydrophilic and are likely to be easier to disperse or dissolve in water. The degree of grafting was in all cases confirmed by FT-IR—the disappearance of the peaks at 1790 and 1830 cm$^{-1}$ from the maleic anhydride was monitored. GPC was used to determine the molecular weight distribution of the resulting products and the amount of free Jeffamine graft. As will be noted from FIGS. 2-5 the reaction of the amine polyethers is very efficient with substantially no or relatively small amounts of free graft compared with the case when hydroxyl polyethers (e.g MPEG, illustrated in FIG. 1). The peak in the GPC traces associated with free graft (retention time between 16 and 17 minutes) is either invisible or very small. This means a smaller quantity of graft needs be added to the reaction to achieve the same degree of grafting, and the process is subsequently more efficient than when MPEG is utilised. Alternatively it is possible to increase the degree of grafting with amine functionalised polyether beyond that which is possible using MPEG. If desired it is still possible to use an excess of Jeffamine (for instance P4 and P8) to increase the probability that every maleic anhydride group and/or acid group is consumed. Unless it is removed by purification this will inevitably lead to a material with a greater percentage of free graft in its composition. Therefore using only a small excess of graft is preferred, using a stoichiometric amount is preferred to a greater degree. Slightly less free graft was observed in the cases where the lower molecular weight amine polyether (P1000) was used. This is due to the tendency of lower molecular weight polymers to react faster than the higher molecular weight species, and this trend is observed with the hydroxyl functionalised PEGs.

The invention claimed is:

1. A method for making a composition comprising an amphiphilic polymeric material that comprises a straight or branched chain carbon-carbon backbone and a multiplicity of side chains attached to the backbone, the method comprising:
    mixing backbone precursors comprising acylating groups with side chain precursors that comprise a nucleophilic group at at least one terminus, to form a reaction mixture;
    heating the reaction mixture;
    stirring the reaction mixture; and
    reacting the nucleophilic groups with the acylating groups to form the amphiphilic polymeric material such that the side chains are linked to the backbone via acyl linkages;
    wherein the reaction mixture does not comprise an organic solvent, and
    wherein each backbone precursor comprises a homopolymer of an ethylenically-unsaturated polymerisable hydrocarbon monomer containing 4 or 5 carbon atoms, said homopolymer having acylating groups grafted thereon.

2. The method according to claim 1, wherein the backbone precursors are mixed with the side chain precursors by dissolving the backbone precursors in molten side chain precursors.

3. The method according to claim 1, wherein the reaction mixture is heated to a temperature in a range of from 100 to 220° C.

4. The method according to claim 1, wherein the reaction mixture is heated in a the presence of an inert gas.

5. The method according to claim 1, further comprising hydrolysing any remaining acylating groups on the backbone to form carboxylic acid groups after the nucleophilic groups have reacted with the acylating groups.

6. The method according to claim 1, wherein polymeric starting materials are mixed using an overhead stirrer, a magnetic stirrer, an extruder, a z-blade mixer, a batch mixer, a U trough mixer, a RT mixer, a compounder, an internal mixer, a two roll mill, a wide blade mixer, a hydrofoil blade mixer, a horizontal delta blade mixer, a horizontal helical blade mixer, a kneader-reactor, a double z-blade mixer, or a twin screw extruder.

7. The method according to claim 1, wherein the acylating groups of the backbone precursors are anhydride groups.

8. The method according to claim 7, wherein the anhydride groups are grafted onto the backbone precursors.

9. The method according to claim 1, wherein the nucleophilic groups are amine groups or hydroxyl groups.

10. The method according to claim 1, wherein the backbone precursors comprise a homopolymer of isobutylene, butadiene, or isoprene.

11. The method according to claim 1, wherein the side chain precursors are derived from poly(ethylene oxide), polyglycine, poly(vinyl alcohol), poly(styrene sulphonate) or poly(acrylic acid).

12. The method according to claim 1 wherein the backbone precursors comprise pendant units of general formula (III):

(III)

wherein:
    $R^3$ is H or C1-6 alkyl,
    $R^5$ is H or C1-6 alkyl, and
    $R^6$ and $R^7$ are H or an acylating group, provided at least one of $R^6$ and $R^7$ is an acylating group, or $R^6$ and $R^7$ are linked to form, together with the carbon atoms to which they are attached, a group of formula (IV):

(IV)

and
the side chain precursors are of general formula (V):

HX$^1$—Y—X$^2$H  (V)

wherein:

$X^1$ is O, S or $NR^4$;

$X^2$ is selected from the group consisting of O, S, $(CH_2)_n$, and $NR^4$;

n is 1-6;

$R^4$ is H or C1-6 alkyl; and

Y is a hydrophilic polymeric group; and in the method, the group $HX^1$ in the compound of formula (V) reacts with units of general formula (III) or (IV) to give the amphiphilic polymeric material having side chains of general formula (I):

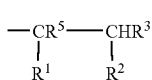

(I)

wherein:

$R^1$ and $R^2$ are each independently H, $-C(O)WR^4$, or $-C(O)Q$, provided that at least one of $R^1$ and $R^2$ is the group $-C(O)Q$; or $R^1$ and $R^2$ together form a cyclic structure together with the carbon atoms to which they are attached, of formula (II):

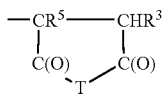

(II)

W is O or $NR^4$;

Q is a group of formula $-X^1-Y-X^2-P$;

T is a group of formula $N-Y-X^2-P$; and

P is H or another backbone.

13. A method for making a comestible comprising:
making a composition comprising an amphiphilic polymeric material according to the method of claim 1; and
adding the composition to a comestible.

14. The method according to claim 13, wherein the comestible is a chewing gum base or a chewing gum composition.

15. The method according to claim 14, wherein:
the comestible is a chewing gum composition,
the composition comprising the amphiphilic polymeric material is used in the formation of a chewing gum base, and
the chewing gum base is mixed with one or more sweetening or flavouring agents to form the chewing gum composition.

16. The method according to claim 15, further comprising adding the amphiphilic polymeric material with the sweetening or flavouring agents to form the chewing gum composition.

17. The method according to claim 14, wherein:
the comestible is a chewing gum composition, and
the composition comprising the amphiphilic polymeric material is mixed with a chewing gum base and one or more sweetening or flavouring agents to form the chewing gum composition.

18. The method according to claim 15, wherein the composition comprising the amphiphilic polymeric material is added to the chewing gum base or the chewing gum composition such that the chewing gum composition comprises 1-90% by weight amphiphilic polymeric material.

* * * * *